(12) United States Patent
Taylor et al.

(10) Patent No.: US 7,318,812 B2
(45) Date of Patent: Jan. 15, 2008

(54) WRIST BRACE HAVING CONTINUOUS LOOP STRAPS AND METHOD OF USING THE SAME

(75) Inventors: Richard G. Taylor, Cincinnati, OH (US); Jessica A. Mills, Mason, OH (US)

(73) Assignee: Beiersdorf, Inc., Cincinnati, OH (US)

( * ) Notice: Subject to any disclaimer, the term of this patent is extended or adjusted under 35 U.S.C. 154(b) by 854 days.

(21) Appl. No.: 10/793,393

(22) Filed: Mar. 4, 2004

(65) Prior Publication Data
US 2005/0197608 A1    Sep. 8, 2005

(51) Int. Cl.
*A61F 5/00* (2006.01)
*A61F 13/00* (2006.01)

(52) U.S. Cl. .......................... 602/211; 602/64

(58) Field of Classification Search .......... 602/20–22, 602/60–64; 128/878, 879; 2/16, 162, DIG. 2, 2/170; 24/442, 444, 683, 684, 686, 265 R, 24/265 H
See application file for complete search history.

(56) References Cited

U.S. PATENT DOCUMENTS

| | | | |
|---|---|---|---|
| 4,537,591 A | 8/1985 | Coates | |
| 4,883,073 A | 11/1989 | Aziz | |
| 4,960,114 A | 10/1990 | Dale | |
| 5,160,314 A | 11/1992 | Peters | |
| 5,415,624 A | 5/1995 | Williams | |
| 5,728,059 A | 3/1998 | Wiesemann et al. | |
| 5,759,166 A | 6/1998 | Nelson et al. | |
| 5,769,804 A | 6/1998 | Harris et al. | |
| 5,916,186 A | 6/1999 | Turto et al. | |
| 5,928,172 A | 7/1999 | Gaylord | |
| 6,013,045 A | 1/2000 | Gaylord | |
| 6,152,891 A | 11/2000 | Carlson | |
| 6,186,969 B1 | 2/2001 | Bell et al. | |
| 6,191,337 B1 | 2/2001 | Himmelsbach | |
| 6,261,253 B1 | 7/2001 | Katzin | |
| 6,561,994 B1 | 5/2003 | Mills et al. | |

FOREIGN PATENT DOCUMENTS

| | | |
|---|---|---|
| EP | 0 809 988 | 12/1997 |
| WO | WO 99/00076 | 1/1999 |
| WO | WO 02/17827 | 3/2002 |

OTHER PUBLICATIONS

PCT Notification of Transmittal of the International Search Report, PCT International Search Report mailed Aug. 23, 2005 for PCT/US2005/005564 (Filed Feb. 22, 2005).

*Primary Examiner*—Kim M. Lewis
(74) *Attorney, Agent, or Firm*—Alston & Bird LLP

(57) ABSTRACT

A reversible wrist brace includes a sheet of flexible material that overlies and supports a wearer's wrist, wherein the sheet of material includes opposing surfaces each having one or more portions of loop material. The flexible sheet has at least one opening in the vicinity of a lateral edge to accommodate at least one fastening strap, such that the strap may slide within the opening. The fastening strap is a continuous loop of sheet material having an outer surface with a hook-bearing portion. The fastener is designed so as to enable a wearer to switch the wrist brace between right and left hands by orienting the hook-bearing portion so that it is coincident with the loop-bearing portion when the wrist brace is worn on either hand. The wrist brace may include a splint that may be inserted within a pocket located on the flexible material to further immobilize the wrist.

18 Claims, 6 Drawing Sheets

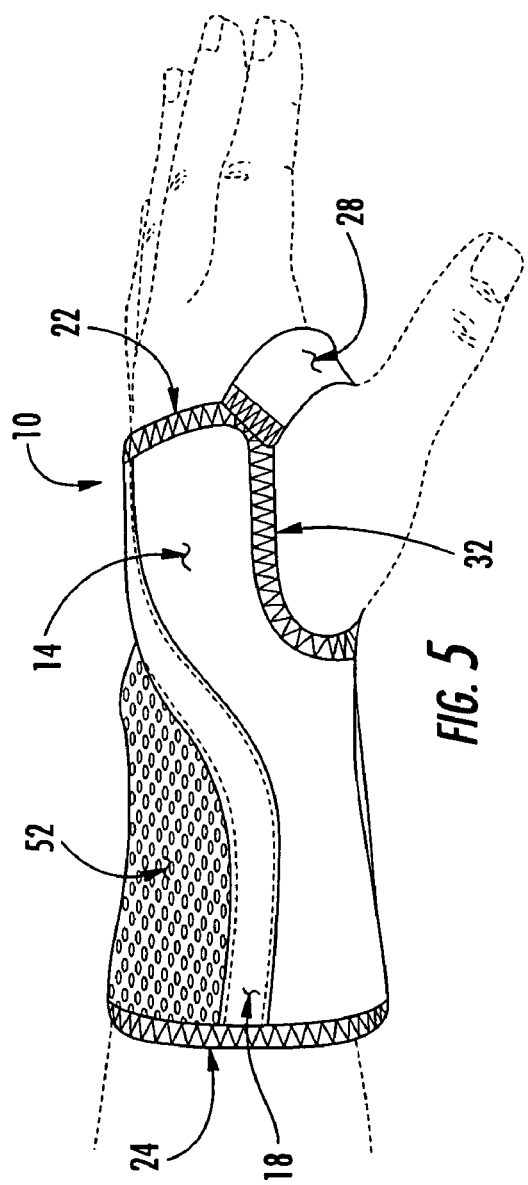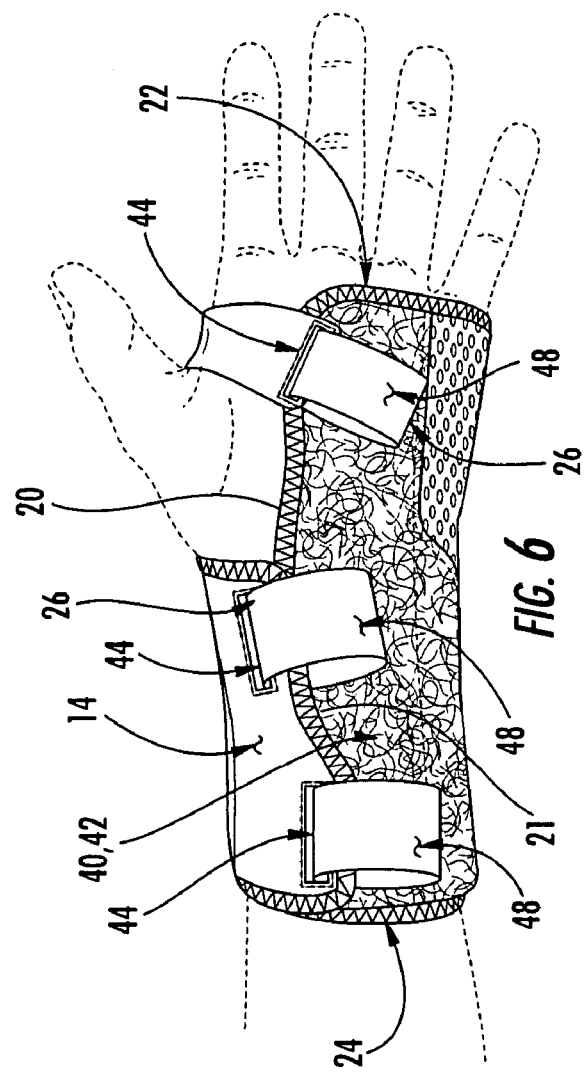

WRIST BRACE HAVING CONTINUOUS LOOP STRAPS AND METHOD OF USING THE SAME

BACKGROUND OF THE INVENTION

1. Field of the Invention

The present invention is related to the field of orthopedic braces, and more particularly, to braces for supporting a wrist joint of a wearer.

2. Description of Related Art

Wrist injuries are relatively common orthopedic injuries that occur in a range of environments, such as a home, office or outdoor environment, and can have varying levels of severity. These levels of severity are routinely grouped into two categories, chronic and acute. Acute injuries occur most often due to sudden impacts that involve the large forces caused by an accident or from a collision during athletic activities. Such traumatic injuries to the wrist typically involve broken bones or sprains. Broken bones are usually treated using complete immobilization, while sprains often only require moderate immobilization for a period of weeks depending on the grade of the sprain. Establishing immobilization early after a sprain ensures that the injury does not evolve into a chronic injury.

Repetitive stresses to the wrist joint are believed to be the most common cause of chronic injuries. Repetitive stresses often occur in an office environment, e.g., typing, or during labor activities, e.g., assembly line work. Given the range of environments and types of injuries that can occur to the wrist, it is advantageous to have wrist braces that provide a range of flexibility and support for the wearer. In addition, due to the reoccurring, extended duration of chronic wrist injuries, a comfortable wrist brace is also desirable.

U.S. Pat. No. 6,561,994 to Mills et al. ("Mills") discloses a wrist brace 10 having both a stretchable portion 12 and a non-stretchable portion 13, as shown in FIG. 1 of Mills. Mills also discloses fasteners having hook or loop material 19, 20, and 21 as well as a longitudinal pocket 22 having a portion of complimentary hook or loop material 22. The wrist brace also includes a splint 30 that may be inserted within the longitudinal pocket 22. The Mills patent is also described as being reversible from either the right or the left hand, at column 2, lines 36-37. A reversible brace enables a wearer to use the same brace for injuries of either the right or left wrists.

The material disclosed in the Mills patent is fabricated of a portion of stretchable material 12 that is capable of stretching to different wearer's wrist sizes when worn. With the fasteners being attached to the elastic material, the wearer can adjust the wrist brace to the desired tension and support depending on the amount of immobilization that is required for a wearer's particular injury. Typically, more immobilization would be required for acute injuries, while less immobilization would be required for chronic injuries so that a wearer can still continue with normal activities while the wrist brace is being worn.

As shown in FIGS. 5-8, the Mills patent also discloses a splint 30 that is formed with a curvature 32 to conform to the wearer's wrist and palm, whereby the splint is inserted into the pocket 22 of the wrist brace, and the wrist support is wrapped around the wearer's wrist and hand and secured with fastening straps 18, 19, and 20. The splint is generally inflexible and provides more immobilization to the wearer's wrist when inserted within the pocket. Thus, the splint would most often be used with acute type injuries, or those chronic injuries where more immobilization is desired.

The various material portions, the fasteners, and the splint provide the versatility to adjust the amount of immobilization depending on the type of injury involved. Mills also discloses a brace that is easy to use given the configuration of the fasteners and flexible material. Despite these improvements, additional innovations in wrist braces to promote better treatment of wrist injuries are also desired.

It would be advantageous to provide a wrist brace that can be adjusted to provide support for a range of injuries, both chronic and acute. In addition, it would be advantageous to have a wrist brace that is easy to use. Finally, it would also be desirable to have a wrist brace that can be used on either a right or left wrist of a wearer.

BRIEF SUMMARY OF THE INVENTION

The above-listed objectives, and other advantages, are achieved by providing a wrist brace of the present invention for supporting a wrist of the wearer. The reversible wrist brace includes a sheet of flexible material that overlies and supports a wearer's wrist, wherein the sheet of material includes opposing surfaces each having one or more portions of loop material. The flexible sheet has at least one opening in the vicinity of a lateral edge to accommodate at least one fastening strap, such that the strap may slide within the opening. The fastening strap is a continuous loop of sheet material having an outer surface with a hook-bearing portion. The fasteners are designed so as to enable a wearer to switch the wrist brace between right and left hands by orienting the hook-bearing portion so that it is coincident with the loop-bearing portion when the wrist brace is worn on either the right or left hand. The wrist brace may include a splint that may be inserted within a pocket located on the flexible material to further immobilize the wrist.

In one embodiment, the present invention includes a reversible wrist brace for alternatively supporting both a right and left wrist of a wearer. The reversible wrist brace comprises a sheet of flexible material. The sheet of material also includes a first surface that is configured to overlie the right wrist of the wearer in a right-handed position and includes a first loop-bearing material portion. The sheet of material further includes a second surface opposite the first surface that is configured to overlie the left hand of the wearer in a left handed position and includes a second loop-bearing material portion. Also included in the sheet of material is a distal edge configured to extend at least partially around the wearer's hand, a proximal edge configured to extend at least partially around the wearer's forearm, and a pair of opposing lateral edges capable of at least partially overlapping each other to extend around the wearer's wrist. In addition, the sheet of flexible material defines at least one opening proximal to one of the lateral edges.

The wrist brace also has at least one fastening strap including a continuous loop of sheet material having an outer surface with a hook-bearing portion and a non-hook bearing portion thereon. The loop of material extends through the opening such that the fastening strap is capable of sliding within the opening to alternate the orientation of the hook-bearing outer surface portion. The hook-bearing portion can be oriented between being coincident with the first surface in the right-handed position, wherein the hook-bearing portion is capable of attaching to the second loop-bearing material portion on the second surface, to being coincident with the second surface in the left-handed position, wherein the hook-bearing portion is capable of attaching to the first loop-bearing material portion on the first surface, and wherein attachment of the hook-bearing portion secures the sheet of flexible material about the wrist.

In another aspect, the hook-bearing portion of the fastening strap comprises at most one half of the outer surface of the fastening strap, such that no portion of the hook-bearing portion is exposed to the wearer when the hook-bearing portion is attached to the first or second loop-bearing portions. The fastening strap may also include an inner surface, opposite to the outer surface of the fastening strap, that is entirely non-hook-bearing material, facilitating free sliding of the fastening strap within the opening. Preferably, the fastening strap has a length of about two inches.

As another option, the wrist brace may include a plurality of openings for accommodating a plurality of straps. For instance, the wrist brace may include three straps wherein a first fastening strap is located near the distal edge, a second fastening strap is located near the proximal edge, and a third fastening strap is located between the first and second fastening straps.

In yet another option, the opening defined proximal to one of the lateral edges has the shape of a slot. The slot may also extend adjacent and generally parallel to its respective lateral edge. Preferably, the slot has a width slightly larger than a width of a corresponding fastening strap and has a height of less than one-eighth of an inch, or slightly more than a thickness of the fastening strap extending therethrough. In this manner, the strap slides freely while still maintaining the orientation of its inner and outer surfaces.

The wrist brace may also include a pocket, running longitudinally between the proximal edge and the distal edge of the sheet of flexible material, secured on either the first or second surfaces and adapted to accommodate a substantially inflexible splint. The splint may also be reversible to fit either the right or left hand.

The present invention has many advantages. The continuous loop construction of the fastening straps allows the wearer to quickly and easily slide the loop through the openings located in the wrist brace to switch between right and left handed positions. The preferred slot shape of the openings, and close fit between the slot shape and the cross-section of the continuous loop of material of the straps, maintains the orientation of the strap during reversal from a left to right handed orientation. Reversal of the hook-bearing portion when the hook bearing portion comprises at most half the outer surface of the fastening strap ensures that the hook-bearing portion is not exposed so as to prevent abrasion of the wearer's skin or snagging on the wearer's clothing. The inner surface of the strap not having non-hook bearing material ensures free sliding of the continuous loop of material within the opening defined by the sheet of material. The use of multiple straps (e.g., three straps) at different positions along a lateral edge of the sheet of flexible material allows adjustment of the amount of support provided by the wrist strap at different locations.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 5 is another perspective view of the wrist brace of FIG. 1;

FIG. 6 is another perspective view the wrist brace of FIG. 1;

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
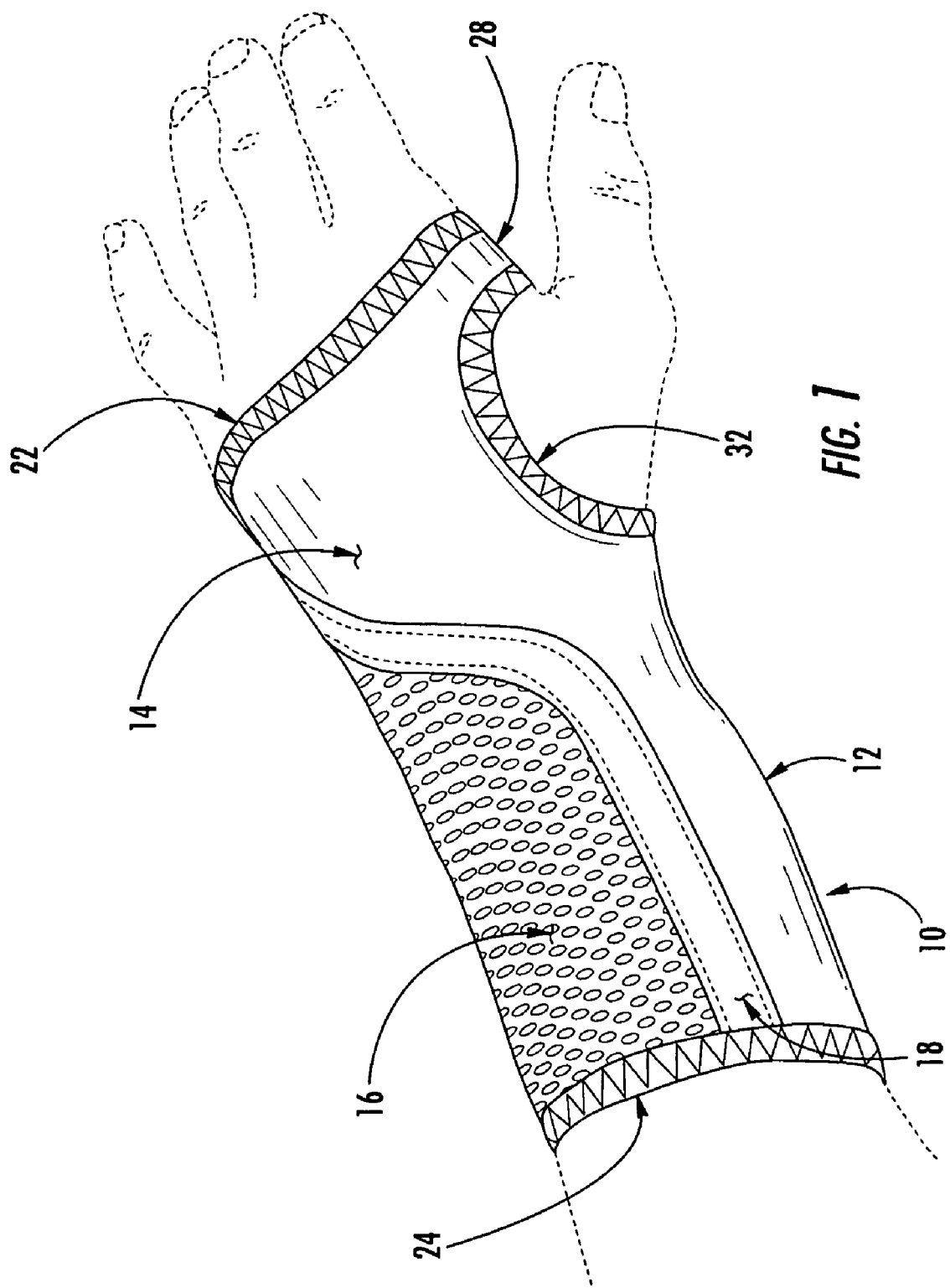
FIG. 1 is a perspective view of a wrist brace of one embodiment of the present invention.
Figure 2:
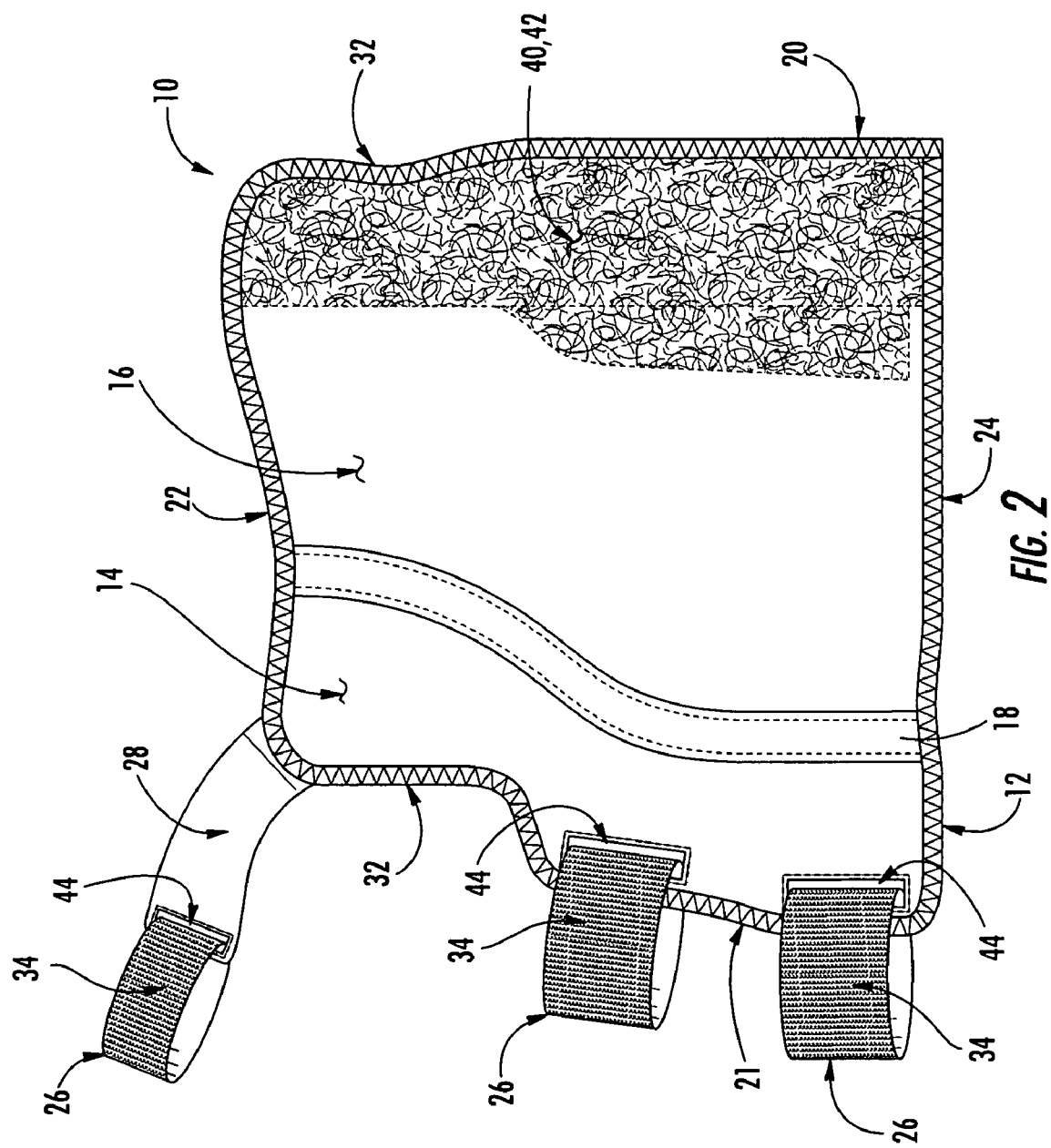
FIG. 2 is a plan view of a first surface of the wrist brace shown in FIG. 1.

One embodiment of a wrist brace 10 of the present invention is shown in FIGS. 1 and 2. The wrist brace 10 includes a sheet 12 of material defined by edges that can extend around the wrist of a wearer. Closure of the sheet of material is secured using a plurality of fastening straps 26. Advantageously, the wrist brace 10 is reversible and can be used on either the right or left wrists of the wearer because of the reversible orientation of the sheet of material 12 and the fastening straps 26, as will be described in more detail below.

Preferably, the sheet of material 12 has a pair of lateral edges 20 and 21, a distal edge 22 and a proximal edge 24. In this manner, when the wrist brace 10 is applied to a wearer's wrist the distal edge 22 extends around the wearer's hand, the proximal edge 24 extends around the wearer's forearm, and the opposing lateral edges 20, 21 overlap each other so as to extend around the wearer's wrist, as is illustrated in FIGS. 1, 5, and 6.

Although the illustrated embodiment shows the sheet of material 12 as having a somewhat rectangular shape with four relatively discrete edges, the sheet of material could have a range of shapes and edge constructions, as long as it is capable of at least partially extending around portions of the hand, arm and wrist. For instance, the sheet of flexible material 12 here could be a circular sheet capable of having only one discrete, circular edge wherein arc-portions of the circular edge extend around the wearer's hand, forearm and wrist and serve as the distal edge 22, the proximal edge 24 and the opposing lateral edges 20, 21.

Optionally, opposite portions of the lateral edges 20 and 21 of the sheet of material 12 (near the distal edge 22) curve inwardly so as to form a pair of inwardly curved edges 32, as shown in FIG. 2. The curved edges 32 form an opening around the wearer's thumb when the remaining portions of the lateral edges 20, 21 are brought together in an adjacent/overlapping arrangement.

In another aspect, the sheet of material 12 may include multiple panels or portions. For instance, in the illustrated embodiment the sheet of material includes a stretchable material portion 14 and a non-stretchable material portion 16, as shown in FIG. 2. The stretchable material portion 14 and non-stretchable material portion 16 have inner edges that are joined along a junction 18 having a spiraled shape. In particular, the spiraled junction is generally closer to the lateral edge 20 at the distal edge 22 of the sheet of material and extends further away from the lateral edge 20 (i.e., towards the opposite lateral edge 21) as it extends toward the proximal edge 24 of the sheet of material. Therefore, in one embodiment, the non-stretchable material portion 16 is wider at the proximal edge 24 than at the distal edge 22.

Figure 3:
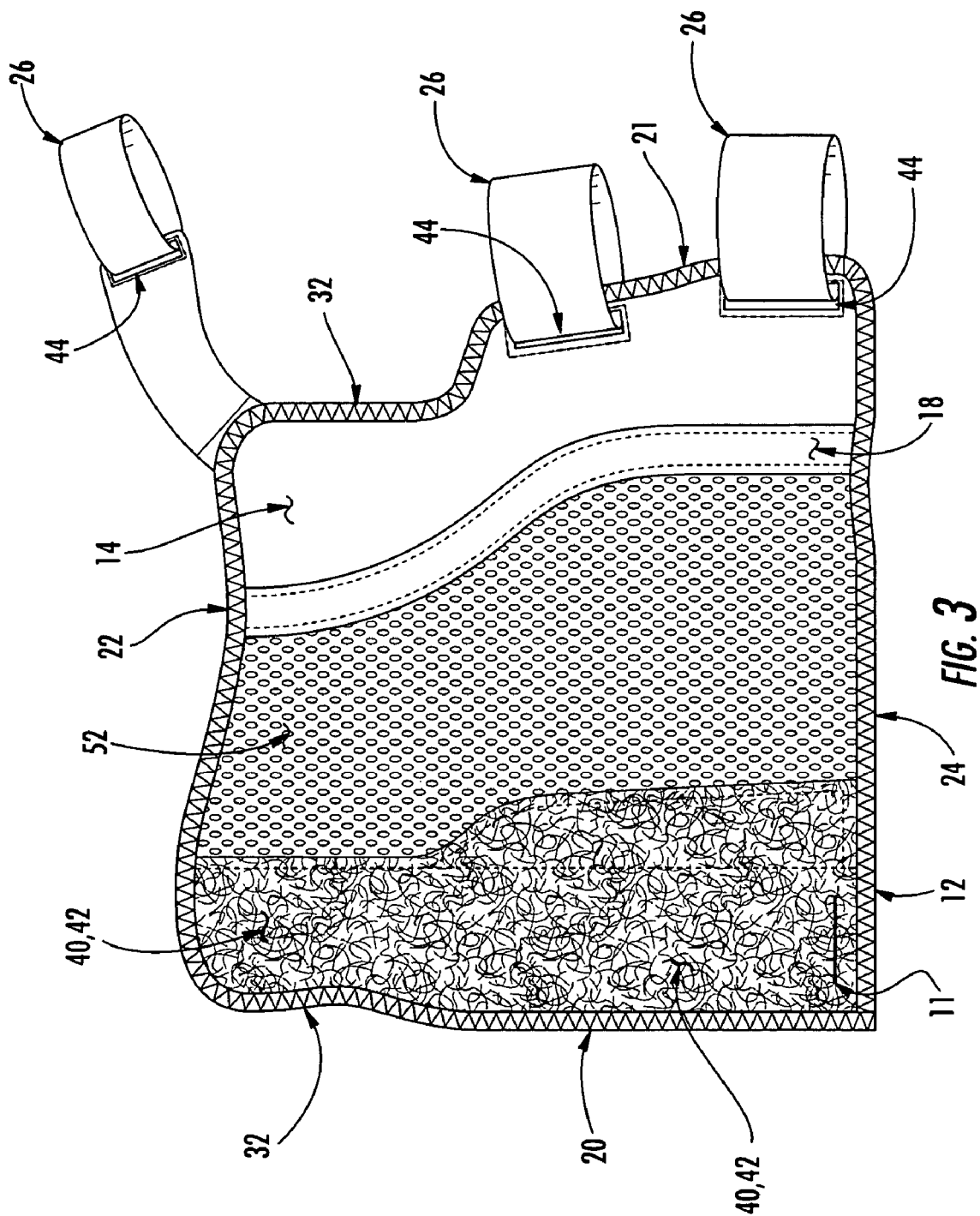
FIG. 3 is a plan view of a second opposite surface of the wrist brace shown in FIG. 1.

The non-stretchable material portion 16 of the wrist brace 10 may be constructed of any fabric that is non-stretchable or substantially non-stretchable, but is preferably made of non-latex material to avoid allergic reactions. Generally, the non-stretchable material portion 16 should be comfortable and breathable so as to wick away moisture from the wearer's hand. As another option, holes 52 may be provided in the non-stretchable material portion 16 to provide additional ventilation and make the material portion even more breathable as shown in FIGS. 3 and 5.

Examples of non-stretchable materials that could be used include material marketed by GEHRING TEXTILES, INC. as SPACER FABRICS, and those marketed by GUILFORD HILLS, INC. as COOL FLEX fabric. Another example of a material or fabric that can be used as the non-stretchable material portion 16 is the warp knitted textile spacer fabric disclosed in U.S. Pat. No. 5,385,036. It should be noted that instead of just a portion, the sheet of material 12 may be entirely formed of a non-stretchable material, especially in circumstances where the wrist brace 10 is custom-fit to an individual wearer.

The stretchable material portion 14 of the wrist brace 10 may be constructed of any variety of flexible and elastic materials so as to promote extension of the fastening straps 26 around the hand and wrist to achieve the desired fit. For instance, the stretchable material portion 14 may be constructed of a fabric that is elastic in one or more directions. Preferably, however, the stretchable material portion 14 is elastic in at least the lateral direction (i.e., between the lateral edges 20, 21) to promote easy extension of the sheet of material 12 about the wrist. As another option, the stretchable material portion 14 may be elastic in both the lateral and longitudinal directions (i.e., between the distal edge 22 and the proximal edge 24). For further comfort, the stretchable material portion 14 may even be elastic in three directions.

Examples of materials well-suited for use in the stretchable material portion 14 are woven, non-woven or knit elastics, neoprene blends, foams, or laminates of the same. Latex materials such as neoprene may be used, but these are preferably avoided to reduce the chance of allergic reactions.

It should be noted that although the illustrated embodiment has stretchable and non-stretchable portions, the entire sheet of material 12 may be formed of a stretchable material, especially in circumstances where fitting of a larger range of hand, wrist and arm sizes is desired. In addition, it should be noted that the sheet of flexible material 12 could include any number of elastic or inelastic material portions as long as it has sufficient overall flexibility to extend around, and provide support for, the wearer's wrist.

As another option, the sheet of material 12 may include a pocket 42 for accommodating an elongated splint 54. The pocket 42 can be located on either side of the sheet of material 12 and is preferably positioned along a lateral edge of the sheet of material opposite to the lateral edge 21 and the fastening straps 26. Preferably, the pocket 42 is sufficiently long in the proximal-distal direction to extend substantially from the proximal edge 24 to the distal edge 22 of the sheet 12 of flexible material. This allows the pocket 42 to accommodate a relatively long elongated splint 54. It should be noted that although the illustrated embodiment is shown as having a pocket 42 and splint 54, the pocket and splint may not even be necessary for wrist brace embodiments where lesser amounts of immobilization are preferred (e.g., for chronic injuries).

Preferably, an opening is defined in the material of the pocket 42 so as to allow insertion, removal, and reversal of the orientation of the elongated splint 54. For instance, in the illustrated embodiment a slit 11 is defined in the pocket 42 adjacent the proximal edge 24, as shown in FIG. 3. Of course the slit or other opening could be defined elsewhere in the pocket 42, but its position in the illustrated embodiment facilitates easy insertion of one end of the elongated splint 54. The slit 11 could also be defined adjacent the distal edge 22 and still advantageously allow similar end-wise insertion of the splint 54.

The pocket 42 is preferably constructed of a non-stretchable material that also acts as a complementary fastening element 40 (e.g., a loop-bearing material) for the fastening straps 26. However, the pocket 42 could also be an elastic or stretchable material that does not act as a fastening element 40. In such a case, a separate complementary fastening element 40 may be attached to the exterior surface of the pocket. As another option, the pocket 42 may not include a complementary fastening element 40 at all if the straps 26 can attach via another mechanism than the hook material, such as an adhesive. For an ambidextrous wrist brace, both sides of the pocket 42 can include the complementary fastening elements 40 so that fastening elements on the fastening straps 26 may attach to either side of the sheet.

Figure 7:
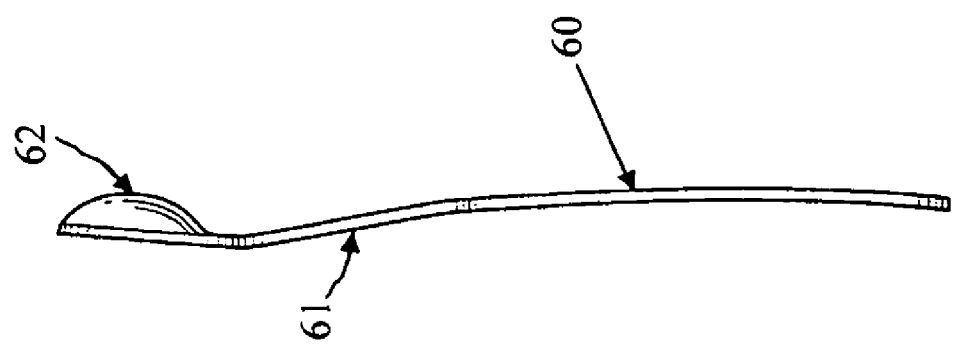
FIG. 7 is a plan view of a splint of the wrist brace of FIG. 1.
Figure 8:
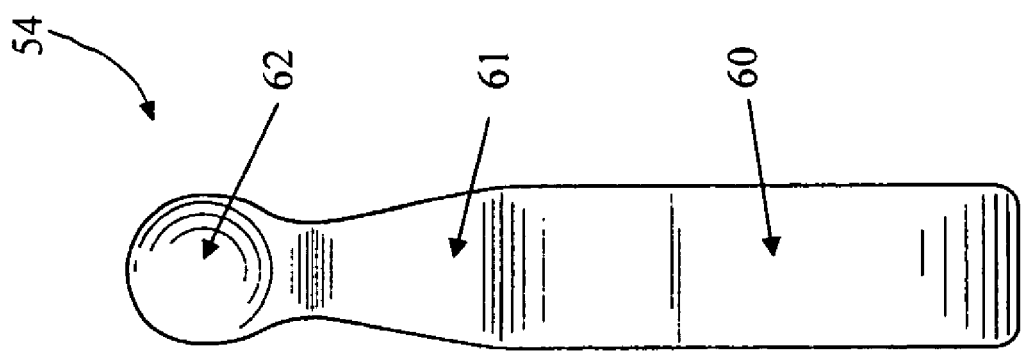
FIG. 8 is a side elevation view of the splint of FIG. 7.

The splint 54 for insertion into the pocket 42 has an elongate shape that includes a planar portion 60, an arc portion 61 and a crown portion 62, as is shown in FIGS. 7 and 8. The preferred splint 54 of the illustrated embodiment is shaped from an elongate, rectangular sheet of rigid material (e.g., aluminum) using a stamping process. The planar portion 60 comprises about half of the length of the splint 54 and generally retains the original, unstamped shape of the sheet of material. The arc portion 61 extends away from the plane of the planar portion in an arc between the planar portion 60 and the crown portion 62. The crown portion 62 has a slightly convex curvature and extends away from the arc portion 61 at an angle more oriented in parallel with the planar portion 60.

The longitudinal and lateral dimensions of the splint 54 are such that the splint extends substantially from the proximal edge 24 to the distal edge 20 along the length of the pocket 42. When the splint 54 is positioned within the pocket 42 the crown and arc portions 62, 61 align with the wearer's palm and wrist, respectively, to maintain the wearer's hand in extension relative to the wrist. The planar portion 60 extends along the wearer's forearm. Such a position is typically considered anatomically neutral so as to reduce strain on the wrist.

It should be noted that if employed, the splint 54 could have any number of shapes, sizes and materials (steel, wood, plastic, etc.) so as to accommodate different wrist sizes, as well as to adjust the desired amount of immobilization. For instance, the splint could be planar along its length, as opposed to the shaped splint of the illustrated embodiments.

Figure 4:
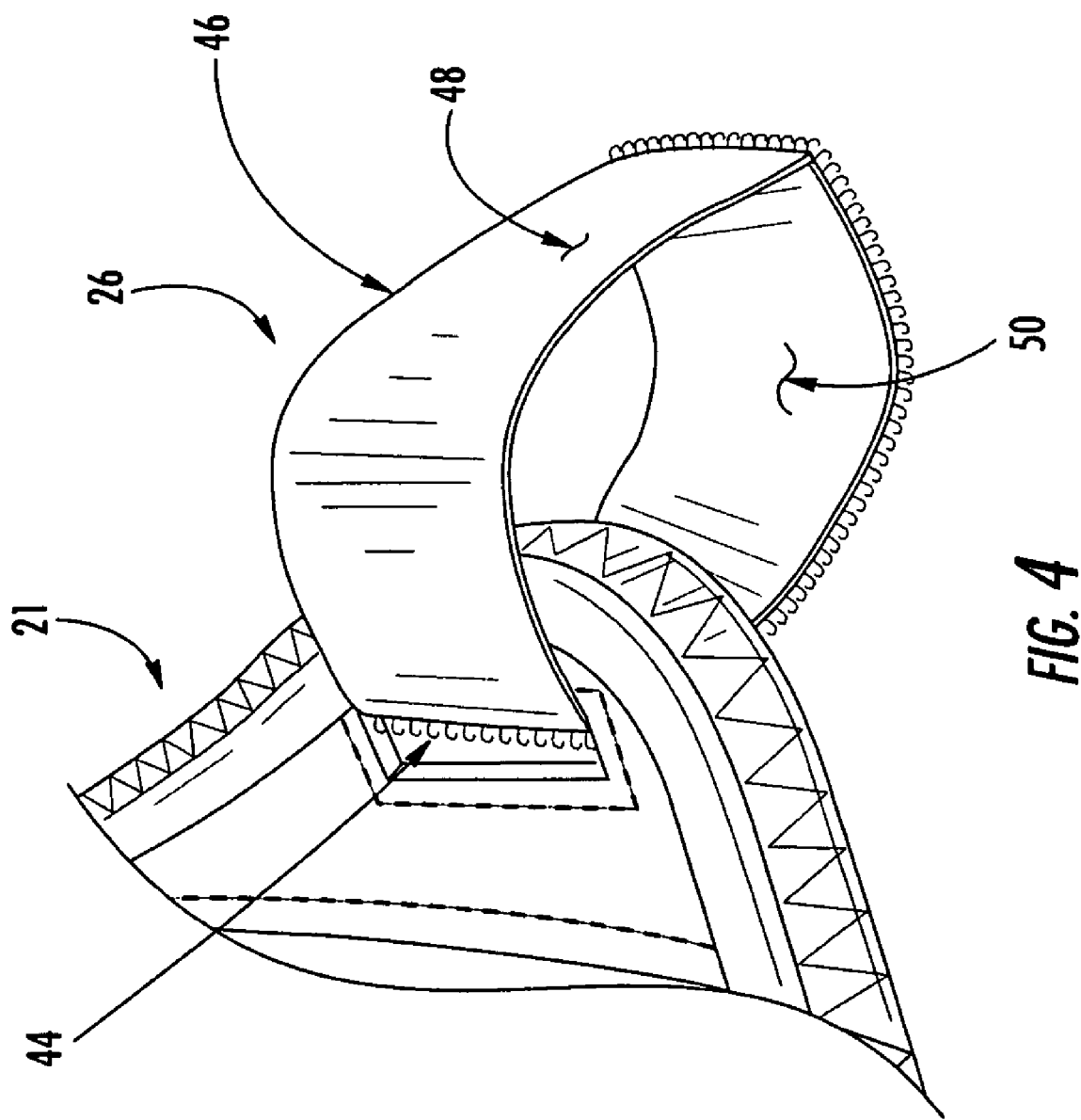
FIG. 4 is an enlarged view of a fastening strap extending through an opening defined in a sheet of material of the wrist brace of FIG. 1.

Each of the fastening straps 26 includes a continuous loop 46 of sheet material that has an outer surface 48 and an inner surface 50, as shown in FIG. 4. In addition, each of the fastening straps 26 is connected to the sheet of material 12 by the continuous loop 46 extending through a respective one of a plurality of openings 44, as shown in FIG. 4.

The continuous loop 46 may be formed by joining the ends of a sheet of material, e.g., such as the elongate rectangular sheet of material of the illustrated embodiment. Joining of the ends can be by stitching, stapling, gluing, etc., as long as the ends are relatively secure against separation when being repositioned and secured to the outer surface of the sheet of material 12. The ends of the continuous loop 46 may also be releasable, such as via the use of a snap or other reusable fastener, to allow replacement of the continuous loop. As another option, the continuous loop 46 may be integrally constructed of a sheet of material that already has a continuous loop structure, such as a circularly knit fabric or an extruded plastic or elastic band. Various types of material, both elastic and inelastic, may be used to construct the continuous loop 46 as long as the continuous loop is sufficiently flexible to slide freely through its respective one of the openings 44.

Fastening by the fastening straps 26 is preferably accomplished via some type of fastening element 34 on the outer surface 48 of the continuous loop 46. In the illustrated embodiments, the fastening element is a hook material that can be connected to the complementary loop material on the pocket 42. Preferably, about half (or less) of the outer surface 48 of the continuous loop 46 is covered with the fastening element 34 while the remaining portion is relatively smooth. With respect to the inner surface 50 of the continuous loop 46, it may be entirely smooth to facilitate sliding. Notably, when tension is exerted on the continuous loop 46, it is the inner surface 50 that is in abutting contact with its respective one of the openings 44, while the fastening element 34 is free from contact due to clearance allowed by the dimensions of the openings, as shown in FIG. 4.

In the illustrated embodiment, the wrist brace 10 is shown as having three fastening straps 26, where a first fastening strap is located near the distal edge 22, a second fastening strap is located near the proximal edge 24, and a third fastening strap is located between the first and second fastening straps. However, the wrist brace 10 of the present invention could have one, two or more than the three fastening straps 26 of the illustrated embodiment, depending upon the size and coverage of the sheet of material 12, the size of the fastening straps themselves, the desired tightness of the fit of the wrist brace, etc. For instance, only a single fastening strap may be needed if the fastening strap is very wide, extending over the entire wrist.

The fastening straps 26 can be any number of lengths or thicknesses depending upon the size of the wearer's wrist, hand and forearm, the number of straps, the dimensions of the sheet of material 12, etc. In the illustrated embodiment the fastening straps are approximately ⅞ of an inch wide and about 2 inches long when flattened which equates to an overall length of the elongated, rectangular sheet of material being about 4 inches (i.e., twice its length when joined in the continuous loop 46). The length of the fastening straps, however, could easily vary between 2 and 3 inches, or lesser/greater, and its width could also easily vary between ½ to 2 inches, or lesser/greater, depending upon the location of the openings 44, size of the wearer, etc. Also, different straps of the same wrist brace 10 could have varying dimensions amongst themselves.

In the illustrated embodiment, the openings 44 are defined in the sheet of material 12 as slots extending adjacent and generally parallel to the lateral edge 21, as shown in FIG. 4. Preferably, each of the openings 44 has a width that is that is slightly longer than a width of its respective one of the fastening straps 26. Additionally, each of the openings 44 are approximately about 1/16 to ⅜ of an inch in height, but preferably ⅛ of an inch to allow the continuous loop 46 and its fastening element 34 to slide freely therein.

The relatively close correspondence in shape and dimensions of the slot shaped openings 44 and the cross-sectional shape and dimensions of the fastening straps 26 advantageously minimizes the likelihood of twisting or changing orientation of the continuous loop 46 while still allowing sufficient clearance for the continuous loop to freely slide. However, it should be noted that the openings can have other shapes and dimensions and still be within the purview of the present invention as long as the continuous loop 46 can slide therein to reverse the orientation of the fastening element 34 disposed thereon. For example, the openings 44 could be circular and have a diameter sufficient to allow the fastening straps 26 to slide freely therein when reversing the orientation of the wrist brace 10.

As shown in FIGS. 2 and 3, the wrist brace 10 may also include a thumb tab 28 that is connected at one end to a corner of the sheet of material 12 between the distal edge 22 and the lateral edge 21. Defined in the opposite end of the thumb tab 28 is one of the openings 44 through which extends the continuous loop 46 of one of the fastening straps 26. Advantageously, the thumb tab 28 is sufficiently long to extend between the thumb and index finger of the wearer so that attachment of the fastening strap can encircle the wearer's thumb, as shown in FIG. 1. The thumb tab 28 may be constructed of a range of flexible materials, such as the stretchable and non-stretchable materials described above for the sheet of material 12. As another option, the thumb tab may be integrally constructed as part of the sheet of material 12, such as part of the stretchable material portion 14.

Preferably, the openings 44 are positioned in a generally parallel orientation with the lateral edge 21 (or the end of the thumb tab 28 if it is employed), as shown in FIGS. 2 and 3. In addition, the openings 44 are positioned relatively close to the lateral edge 21 in the illustrated embodiment. Such positioning allows for the continuous loop 46 to have a relatively short length and still extend past the lateral edge 21 and onto the sheet of material 12 for attachment. Also, the relatively parallel alignment of the openings 44 and lateral edge 21 allow the straps 44 to extend perpendicularly out from the adjacent portions of the lateral edge.

In the illustrated embodiment, the fastening elements 34 located on the outer surface of the fastening straps 26, as well as the fastening elements 40 located on either side of the sheet of material 12, are constructed of a complementary hook and loop material such as VELCRO®. However, the term "fastening element" as used herein denotes any type of chemical, mechanical or other fastener that allows connection of two separate components, such as snaps, hook and loop connectors, adhesives, buckles, etc. Notably, the fastening elements 34 (hooks) located on the outer surface of the fastening straps 26 and the fastening elements 40 (loops) located on the sheet of material 12 mate to and attach with one another when brought into contact. These fastening elements 34, 40, therefore, are referred to herein as being complementary.

During use, the wrist brace 10 is taken from a flat configuration (as shown in FIGS. 2 and 3) and applied to the hand, wrist and forearm of the wearer (as shown in FIGS. 1, 5 and 6). Application of the sheet of material 12 about the wrist of the wearer includes overlapping one of the lateral edges (e.g., lateral edge 21) over the other one of the lateral edges (e.g., lateral edge 20). In addition, the thumb tab 28 is extended between the thumb and index finger of the wearer.

Once the sheet of material 12 and thumb tab 28 have been at least partially applied to the wearer's anatomy, the fastening elements 34 on the outer surface of the fastening straps 26 are pulled to the point of desired tension and secured to the complementary fastening elements 40 on the surface of the sheet of material. The optional splint 54 may also be inserted into the pocket 42 through the slit 11 if not already within the pocket for further support of the wearer's wrist.

Reversal of the wrist brace 10 to the opposite hand includes removal of the fastening straps 26 from the surface of the sheet of material 12 and the sheet of material from the wearer's hand, wrist, and arm. Then, the splint 54 is removed from the pocket 42. Each of the fastenings straps 26 is then reoriented by sliding the continuous loop 46 of the fastening strap within its respective one of the openings 44 until the fastening element 34 on its outer surface is coincident with the surface of the sheet of material 12 to be applied adjacent the wearer's hand, wrist, and arm. In this manner, when the lateral edges are overlapped, the fastening elements 34 can attach directly to the complementary fastening elements 40 on the newly reversed outer surface of the sheet of material 12. Advantageously, the fastening elements 34 which cover less than half the outer surface 48 of the continuous loop 46 are not free to snag on clothing or irritate the skin.

The present invention has many advantages. The continuous loop 46 of each of the fastening straps 26 allows the wearer to quickly and easily slide the continuous loop through its respective one of the openings 44 when switching between right and left handed positions. The preferred slot shape of the openings 44, and close fit between the slot shape and the cross-section of the continuous loop 46 of the fastening straps 26, maintains the orientation of the straps during reversal of the wrist brace between the left and right wrists. Reversal of the hook-bearing portions, or other fastening elements 34, when the hook bearing portion comprises at most half the outer surface of the fastening strap ensures that the hook-bearing portion is not exposed. This prevents abrasion of the wearer's skin or snagging of the wearer's clothing. The inner surface of each of the fastening straps 26 not having non-hook bearing material ensures free sliding of the continuous loop 46 within a respective one of the openings 44 defined by the sheet of material 12. The use of multiple fastening straps 26 (e.g., three straps) at different positions along the lateral edge 21 of the sheet of flexible material 12 allows adjustment of the amount of support provided by the wrist strap 10 at different locations.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A reversible wrist brace for alternatively supporting both a right and a left wrist of a wearer, said reversible wrist brace comprising:

a sheet of flexible material having a first surface that is configured to overlie the right wrist of the wearer in a right handed position and includes a first loop-bearing material portion, a second surface opposite the first surface that is configured to overlie the left wrist of the wearer in a left handed position and includes a second loop-bearing material portion, a distal edge configured to extend at least partially around the wearer's hand, a proximal edge configured to extend at least partially around the wearer's forearm, and a pair of opposing lateral edges capable of at least partially overlapping each other to at least partially cover the wearer's wrist, wherein said sheet of flexible material defines at least one opening proximal to one of the lateral edges; and at least one fastening strap including a continuous loop of sheet material having an outer surface with a hook-bearing portion and non-hook bearing portion, said continuous loop of material extending through said opening such that said fastening strap is capable of sliding within the opening to alternate orientation of the hook-bearing outer surface between being coincident with the first surface in the right-handed position, wherein the hook-bearing portion is capable of attaching to the second loop-bearing material portion on the second surface, to being coincident with the second surface in the left-handed position, wherein the hook-bearing portion is capable of attaching to the first loop-bearing material portion on the first surface, wherein attachment of the hook-bearing portion secures the sheet of flexible material about the wrist.

2. A wrist brace of claim 1, wherein said hook-bearing portion comprises at most one half of said outer surface of said fastening strap, such that no portion of said hook-bearing portion is exposed to said wearer when said hook-bearing portion is attached to said first or second loop-bearing material portions.

3. A wrist brace of claim 1, wherein an inner surface, opposite said outer surface of said fastening strap, is entirely non-hook-bearing material.

4. A wrist brace of claim 1, further comprising a second and third fastening strap, and a second and third opening, wherein said first fastening strap and first opening are located near said distal edge, said second fastening strap and second opening are located near said proximal edge, and said third fastening strap and third opening are located between said first and second fastening straps.

5. A wrist brace of claim 4, wherein said fastening straps have a length of approximately two inches.

6. A wrist brace of claim 4, wherein each of said openings has a width slightly larger than a width of a corresponding one of said fastening straps extending therethrough.

7. A wrist brace of claim 1, wherein said opening has a slot shape.

8. A wrist brace of claim 7, wherein said slot extends adjacent and generally parallel to its respective one of the lateral edges.

9. A wrist brace of claim 1, wherein said opening is less than one-eighth of an inch in height and is slightly wider than a thickness of said fastening strap.

10. A wrist brace of claim 1, further comprising a pocket extending between the proximal edge and the distal edge of said sheet of flexible material, secured on one of said first and second surfaces and sized to receive a splint.

11. A reversible wrist brace for alternatively supporting both a right and left wrist of a wearer, said reversible wrist brace comprising:

a sheet of flexible material having a first surface that is configured to overlie the right wrist of the wearer in a right handed position and includes a first fastening element, a second surface opposite the first surface that is configured to overlie the left hand of the wearer in a left handed position and includes a second fastening element, a distal edge configured to extend at least partially around the wearer's hand, a proximal edge configured to extend at least partially around the wearer's forearm, and a pair of opposing lateral edges capable of at least partially overlapping each other to at least cover the wearer's wrist, wherein said sheet of flexible material defines at least one slot having a length extending adjacent and generally parallel to one of the lateral edges; and at least one fastening strap including a continuous loop of sheet material having a width at most equal to the width of the slot and an outer surface having a complementary fastening element covering at most one-half of said outer surface and capable of attaching to said first and second fastening elements, said loop of material extending through said slot so as to be capable of sliding within the slot to alternate orientation of the complementary fastening element between being coincident with the first surface in the right-handed position and capable of attaching to the second fastening element on the second surface, to being coincident with the second surface in the left-handed position and capable of attaching to the first fastening element on the first surface, wherein attachment of the fastening elements secures the sheet of flexible material about the wrist and conceals the complementary fastening element.

12. A wrist brace of claim 11, wherein an inner surface, opposite said outer surface of said fastening strap is entirely non-fastening material.

13. A wrist brace of claim 11, further comprising a second and third fastening strap, and a second and third slot, wherein said first fastening strap and first slot are located near said distal edge, said second fastening strap and second slot are located near said proximal edge, and said third fastening strap and third slot are located between said first and second fastening straps.

14. A wrist brace of claim 13, wherein said fastening strap has a length of approximately two inches.

15. A wrist brace of claim 13, wherein each of said slots has a width slightly larger than a width of a corresponding one of said fastening straps extending therethrough.

16. A wrist brace of claim 11, wherein said first and second fastening elements on said sheet include a loop-bearing material and said complementary fastening element on said outer surface of said fastening strap includes a hook-bearing material.

17. A wrist brace of claim 11, wherein said slot is less than one-eighth of an inch in height and is slightly wider than a thickness of said fastening strap.

18. A wrist brace of claim 11, further comprising a pocket extending between said proximal edge and said distal edge of said sheet of flexible material, secured on one of said first and second surfaces and sized to receive a substantially inflexible splint.

* * * * *